United States Patent [19]

Mattalia

[11] 4,001,228
[45] Jan. 4, 1977

[54] 2-THIOL-4,5-DIPHENYLOXAZOLE S-DERIVATIVES

[75] Inventor: Gabriele Mattalia, Rome, Italy

[73] Assignee: Serono Laboratories, Inc., Boston, Mass.

[22] Filed: July 23, 1975

[21] Appl. No.: 598,186

[30] Foreign Application Priority Data

Aug. 6, 1974 United Kingdom ............. 34673/74

[52] U.S. Cl. .................. 260/247.1 M; 260/293.67; 260/307 R; 424/267; 424/272; 424/248.52
[51] Int. Cl.² ...................................... C07D 263/46
[58] Field of Search .............. 260/307 R, 247.1 M, 260/293.67; 424/272, 248, 267

[56] References Cited

OTHER PUBLICATIONS

Derible et al. C.A. 79, 126485m (1973).
Wagner et al., "Synthetic Organic Chemistry" 1953, John Wiley & Sons, New York, p. 787.

*Primary Examiner*—R. J. Gallagher
*Attorney, Agent, or Firm*—Ostrolenk, Faber, Gerb & Soffen

[57] ABSTRACT

This invention relates to certain 2-thiol-4,5-diphenyloxazole S-derivatives, to processes for their preparation and to therapeutic compositions containing them.

6 Claims, No Drawings

2-THIOL-4,5-DIPHENYLOXAZOLE S-DERIVATIVES

DESCRIPTION OF THE INVENTION

According to the present invention, there is provided a 2-thiol-4,5-diphenyloxazole S-derivative of the formula:

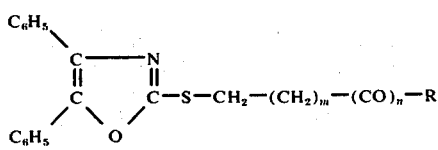

wherein $m$ is 0, 1 or 2, $n$ is 0 or 1 and R represents hydroxy, alkoxy, amino, alkylamino, heterocyclic amino, aminoalkoxy, alkylaminoalkoxy or heterocyclic aminoalkoxy radical wherein the alkyl chains have from 1 to 4 carbon atoms and the heterocyclic amino rings have 5 or 6 ring members and are attached via the nitrogen atom. Also included within the scope of this invention are salts of the compounds of formula (I) above, particularly pharmaceutically acceptable addition salts thereof.

Examples of specific sub-classes of compounds included within the present invention and covered by the scope of the general formula (I) are as follows:

S-(4,5-diphenyloxazol-2-yl)-mercaptocarboxylic acids of the formula:

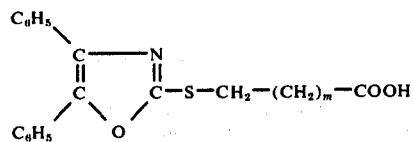

wherein $m$ is 0, 1 or 2, and pharmaceutically acceptable lower alkyl esters and salts thereof;

S-(4,5-diphenyloxazol-2-yl)-mercaptocarboxylic acid amides of the formula:

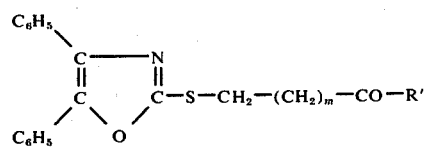

wherein $m$ is 0, 1 or 2 and R' represents amino, alkylamino or a heterocyclic amino radical as defined above with reference to general formula (I), and pharmaceutically acceptable acid addition salts thereof;

S-(4,5-diphenyloxazol-2-yl)-mercaptocarboxylic acid esters of the formula:

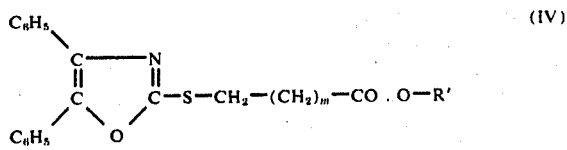

wherein $m$ is 0, 1 or 2 and R'' represents aminoalkyl, alkylaminoalkyl or a heterocyclic amino alkyl radical wherein the alkyl chains and the heterocyclic amino rings are as defined above with reference to general formula (I), and pharmaceutically acceptable acid addition salts thereof;

2-aminoalkylthio-4,5-diphenyloxazoles of the formula:

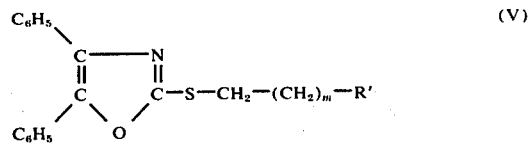

wherein $m$ is 0, 1 or 2 and R' is as defined above with reference to formula (III), and pharmaceutically acceptable acid addition salts thereof;

2-oxyalkylthio-4,5-diphenyloxazoles of the formula:

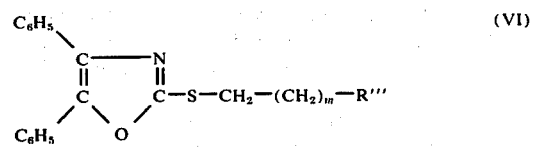

wherein $m$ is 0, 1 or 2 and R''' represents hydroxy or alkoxy as defined above with reference to general formula (I).

A particularly preferred class of compounds is that defined by formula (II) above. The compounds of formula (II) not only exhibit strong pharmacological activity as shown below, but also are useful as intermediates in the synthesis of other compounds of formula (I), especially those identified by the formulae (III) and (IV).

Especially preferred for therapeutical purposes are the addition salts of the S-(4,5-diphenyloxazol-2-yl)-mercaptocarboxylic acids of formula (II) with organic bases, said salts having the general formula:

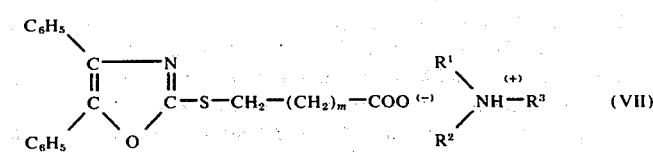

wherein m is 0, 1 or 2 and $R^1$, $R^2$ and $R^3$ are hydrogen or alkyl or hydroxyalkyl having from 1 to 4 carbon atoms.

In contrast with the insolubility of most of the compounds of formula (I), the addition salts of formula (VII) are more likely to be soluble and, in general, are preferred for administration as therapeutic agents. Some of the esters of formula (IV) have also been found to be soluble.

As shown by tests on laboratory animals, the compounds of this invention are mainly characterized by a strong inhibitory action on platelet aggregation, often associated with other therapeutic activities.

Accordingly, the invention further provides a pharmaceutical composition comprising one or more of the compounds of formula (I) as defined above, or a salt or salts thereof, and a pharmaceutically acceptable diluent, carrier or excipient.

The starting material for the synthesis of compounds of formula (I) is 2-thiol-4,5-diphenyloxazole or 4,5-diphenyl-4-oxazolin-2-thione. This compound exhibits tautomerism, that is, it reacts in isomeric structures which differ from each other in the position of a hydrogen atom and a double bond:

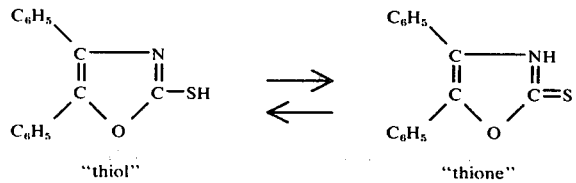

"thiol"           "thione"

All of the compounds of formula (I) above are derivatives of the "thiol" form. Therefore, an alkali metal salt of 2-thiol-4,5-diphenyloxazole may be used in place of the free thiol or thione as the starting material in the process of this invention, the tautomeric equilibrium having been shifted towards the thiol form because of salt formation.

Thus, the invention provides a process for preparing a compound of formula (I), which process comprises reacting 2-thiol-4,5-diphenyloxazole or an alkali metal salt thereof with a compound of the formula:

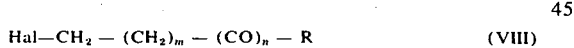
Hal—CH$_2$ — (CH$_2$)$_m$ — (CO)$_n$ — R     (VIII)

wherein m and n are as defined above with reference to general formula (I), Hal represents a halogen atom and R is as defined in connection with formula (I), with the proviso that when n is 1, R may not represent hydroxy and when a compound of formula (I) is required in which n is 1 and R represents hydroxy, a compound of formula (I) wherein R represents alkoxy is, if appropriate, hydrolyzed to the free acid.

Operational particulars, such as the choice of the solvent and the reaction temperature and time, may be selected by those skilled in the art. A man skilled in the art will be able to select the most appropriate conditions for a specific reaction from a reading of the specific Examples given hereinafter.

The invention also provides a process which permits an acid of formula (II) to be directly prepared. As stated above, the acids of formula (II) may be prepared by hydrolyzing an ester obtained by carrying out the general process of the invention. However, hydrolysis of the ester is not always desirable or even possible. For example, alkaline hydrolysis of ethyl S-(4,5-diphenyloxazol-2-yl)-mercaptopropionate gave 2-thiol-4,5-diphenyloxazole instead of the desired S-(4,5-diphenyloxazol-2-yl)-mercaptopropionic acid. In such cases, direct synthesis of the free acids appears, in practice, to be the only available means for preparing them.

Thus, the invention provides a process for the preparation of a compound of formula (II), which process comprises reacting an alkali salt of 2-thiol-4,5-diphenyloxazole with an alkali metal salt of a haloalkyl-carboxylic acid of the formula:

Hal — (CH$_2$)$_m$ — COOH     (IX)

wherein m is as defined above and Hal represents halogen.

Although the reaction does not appear to require a specific solvent, best results have been obtained using N,N-dimethylformamide as the reaction medium.

Certain alternative procedures are available for preparing the compounds of general formula (I). Some of these procedures are listed below and are specifically illustrated in the following Examples, such procedures being included in the present invention:

a. Preparing the amides of formula (III) by reacting an acid of formula (II) with the appropriate amine;
b. Preparing the esters of formula (IV) by esterifying an acid of formula (II) with the appropriate aminoalcohol;
c. Preparing the esters of formula (IV) by condensing an acid of formula (II) with the appropriate aminoalcohol in the presence of N,N'-dicyclohexylcarbodiimide; and
d. Using 2-chloro-4,5-diphenyloxazole as the starting material for the preparation of any of the compounds of formula (I) in the place of 2-thiol-4,5-diphenyloxazole or an alkali metal salt thereof, and reacting the chloro-oxazole with the appropriate mercaptan.

The following Examples are given to further illustrate and describe the present invention.

ETHYL S-(4,5-DIPHENYLOXAZOL-2-YL)-MERCAPTOACETATE

In a three-necked, 500 ml flask provided with reflux condenser and mechanical stirrer, 25.3 g 4,5-diphenyl-4-oxazolin-2-thione, 27.6 g anhydrous potassium carbonate, 14.5 ml ethyl bromoacetate and 200 ml absolute ethanol were refluxed for 5 hours with vigorous stirring. The mixture was cooled to room temperature, filtered and washed with absolute ethanol on the filter. The filtrate was evaporated to dryness in vacuo and the residue was suspended in 150 ml ether and 150 ml water. The ethereal phase was separated, dried on anhydrous sodium sulphate, filtered and evaporated to dryness in vacuo to give 23 g ethyl S-(4,5-diphenyloxazol-2-yl)-mercaptoacetate as an oil which was recrystallized from an anhydrous ether-petroleum ether mixture: m.p. 53°–55° C; yield = 67.9%.

EXAMPLE 2

S-(4,5-DIPHENYLOXAZOL-2-yl)-MERCAPTOACETIC ACID.

10 g ethyl S-(4,5-diphenyloxazol-2-yl)-mercaptoacetate dissolved in 30 ml ethanol were mixed with 30 ml 40% NaOH and maintained for 1 hour at room temperature. The sodium salt which separated from the reaction mixture was redissolved by means of addition of 200 ml distilled water. The alkaline solution was slowly poured into 300 ml ice-cooled 15% HCl. The precipitated S-(4,5-diphenyloxazol-2-yl)-mercaptoacetic acid was filtered, washed with water and crystallized from aqueous ethanol to give 7.4 g of a product melting at 137°–139° C (yield = 80.7%).

Analysis: Calc. for $C_{17}H_{13}O_3NS$: C = 65.58%; H = 4.21%; Found: C = 65.51%; H = 4.30%.

2-DIMETHYLAMINOETHANOL SALT OF S-(4,5-DIPHENYLOXAZOL-2-YL)-MERCAPTOACETIC ACID.

6.2 g S-(4,5-diphenyloxazol-2-yl)-mercaptoacetic acid and 8.9 g 2-dimethylaminoethanol were dissolved in 10 ml absolute ethanol and the solution was kept for 1 hour at room temperature and then evaporated to dryness in vacuo. The oily residue was suspended in anhydrous ether, whereby a crystalline solid slowly separated from the mixture. The solid was filtered and crystallized from a methanol-anhydrous ether mixture to give 6.5 g of water-soluble 2-dimethylaminoethanol salt of S-(4,5-diphenyloxazol-2-yl)-mercaptoacetic acid, melting at 66°–68° C (yield 81.2%).

The analysis indicated a 1:1 ratio between the acid and 2-dimethylaminoethanol.

Analysis: Calc. for $C_{21}H_{24}O_4N_2S$: C = 62.97%; H = 6.04%; Found: C = 62.99%; H = 5.87%.

EXAMPLE 4

METHYLAMINOETHANOL SALT OF S-(4,5-DIPHENYLOXAZOL-2-YL)-MERCAPTOACETIC ACID.

By following the same procedure as in Example 3, the methylaminoethanol salt of S-(4,5-diphenyloxazol-2-yl)-mercaptoacetic acid was obtained from S-(4,5-diphenyloxazol-2-yl)-mercaptoacetic acid and 2-methylaminoethanol. The product was crystallized from a methanol-anhydrous ether mixture and showed a melting point of 69°–71° C.

Analysis: Calc. for $C_{20}H_{22}O_4N_2S$: C = 62.15%; H = 5.74%; Found: C = 61.89%; H = 5.84%.

EXAMPLE 5

2-DIMETHYLAMINOETHYL S-(4,5-DIPHENYLOXAZOL-2-YL)-MERCAPTOACETATE.

6.2 g S-(4,5-diphenyloxazol-2-yl)-mercaptoacetic acid and 1.8 g 2-dimethylaminoethanol dissolved in 24 ml tetrahydrofuran were mixed with 4.73 g N,N'-dicyclohexylcarbodiimide dissolved in 20 ml tetrahydrofuran. The mixture was kept for 15 hours at room temperature with stirring in a sealed flask.

A precipitate formed consisting of N,N'-dicyclohexylurea, which was separated by filtration and washed on the filter with 40 ml tetrahydrofuran. The filtrate was evaporated to dryness in vacuo, the residue was carefully triturated in the presence of 200 ml anhydrous ether and filtered to quantitatively remove the N,N'-dicyclohexylurea, after which the filtrate was evaporated to dryness and redissolved in 14 ml absolute ethanol. The solution was treated with 4 ml 30% HCl alcohol solution and then with 100 ml anhydrous ether to give 4.6 g 2-dimethylaminoethyl S-(4,5-diphenyloxazol-2-yl)-mercaptoacetate hydrochloride which was purified by crystallization from a methanol-anhydrous ether mixture. The water soluble product melted at 137°–139° C (yield = 55.2%).

Analysis: Calc. for $C_{21}H_{23}O_3N_2S$: C = 60.20%; H = 5.53%; Found: C = 60.27%; H = 5.60%.

EXAMPLE 6

2-MORPHOLINOETHYL S-(4,5-DIPHENYLOXAZOL-2-YL)-MERCAPTOACETATE 95.2 g 2-morpholinoethanol was first prepared by reacting 87.12 g morpholine and 80.5 g ethylene chlorohydrin in the presence of 151.8 g triethylamine and 200 ml anhydrous benzene.

In a 500 ml, three-necked flask, 3.1 g S-(4,5-diphenyloxazol-2-yl)-mercaptoacetic acid and 3.9 g 2-morpholino ethanol were dissolved in 200 ml anhydrous benzene. 10 ml concentrated $H_2SO_4$ were dropped into the mixture that was then refluxed for 8 hours. After cooling, 200 ml water were added and the aqueous phase was separated from the benzene phase in a separatory funnel.

The aqueous phase was alkalinized with 5% NaOH and extracted with ether. The benzene phase was washed with 5% NaOH and then washed twice with water, after which it was dried over anhydrous $Na_2SO_4$ and filtered. The washed and dried benzene phase was mixed with the ethereal extract of the aqueous phase, and the whole mixture was evaporated to dryness to give an oily residue which was heated for 1 hour on a steam bath under vacuum. The residue was then redissolved in 10 ml methanol, filtered, treated with 3 ml 30% HCl alcohol solution and then with anhydrous ether. A crystalline solid was obtained consisting of 2-morpholinoethyl S-(4,5-diphenyloxazol-2-yl)-mercaptoacetate hydrochloride. After recrystallization from a methanol-anhydrous ether mixture the product melted at 155°–156° C. Yield = 47.8%.

Analysis: Calc. for $C_{23}H_{24}O_4N_2S.HCl$: C = 59.92%; H = 5.46%; Found: C = 59.31%; H = 5.56%.

The title compound was also prepared by an alternative route consisting in first preparing 24.4 g 2-morpholinoethyl chloroacetate hydrochloride from 26.2 g 2-morpholinoethanol and 22.6 g chloroacetyl chloride.

A 7.3 g aliquot of the thus prepared 2-morpholinoethyl chloroacetate hydrochloride was then reacted according to the procedure of Example 1 with 7.6 g 4,5-diphenyl-4-oxazolin-2-thione to give 2.4 g of the title compound.

EXAMPLE 7

ETHYL 3-S-(4,5-DIPHENYLOXAZOL-2-YL)-MERCAPTOPROPIONATE

The potassium salt of 2-thiol-4,5-diphenyloxazole was first prepared by hot dissolving the oxazole (70 g) in 700 ml 10% $K_2CO_3$. The salt crystallized from the solution and was recovered by filtration.

58.2 g of the thus prepared potassium salt of 2-thiol-4,5-diphenyloxazole were suspended in 300 ml N,N- dimethylformamide and treated with 72.4 g ethyl 3-bromopropionate. The reaction mixture was kept for 12 hours at room temperature under vigorous stirring and then poured into 1000 ml water containing crushed ice. Ethyl β-S-(4,5-diphenyloxazol-2-yl)-mercaptopropionate quickly crystallized from the solution. After filtering and re-crystallizing from aqueous ethanol, a product was obtained melting at 66°–67° C. Yield = 89.9%.

Analysis: Calc. for $C_{20}H_{19}O_3NS$: C = 67.95%; H = 5.42%; Found: C = 67.65%; H = 5.36%

EXAMPLE 8

3-S-(4,5-DIPHENYLOXAZOL-2-YL)-MERCAPTOPROPIONIC ACID

The sodium salt of β-chloropropionic acid was first prepared by reacting in methanol solution 94.7 g β-chloropropionic acid and 34.9 g NaOH for two hours at room temperature.

By a separate procedure, the potassium salt of 2-thiol-4,5-diphenyloxazole was also prepared as described in the first paragraph of Example 7 above.

57.3 g potassium salt of 2-thiol-4,5-diphenyloxazole and 30 g sodium salt of β-chloropropionic acid were dissolved in 200 ml N,N-dimethylformamide and stirred for 1 hour at room temperature. The temperature of the reaction mixture was then brought to 100° C for 20 minutes. After cooling, 2000 ml distilled water were added and the mixture was acidified with HCl to obtain an oily precipitate which was extracted with ether.

The etheral phase was extracted twice with 200 ml 5% NaOH, the alkaline extracts were collected, filtered and acidified with 50% HCl to obtain an oil which slowly crystallized. After recrystallization from aqueous methanol, a product was obtained melting at 110°–112° C or 128°–130° C (the difference in melting points was probably due to allotropism). Yield = 62.4 g (64%).

Analysis: Calc. for $C_{18}H_{15}O_3NS$: C = 66.44%; H = 4.65%; Found: C = 66.35%; H = 4.67%

By using the techniques of the preceding Examples, the following compounds were synthesized and identified.

a) 2-morpholinoethyl 3-S-(4,5-diphenyloxazol-2-yl)-mercaptopropionate  m.p. 145°–147° C
b) 2-dimethylaminoethyl 3-S-(4,5-diphenyloxazol-2-yl)-mercaptopropionate  m.p. 98°–101° C
c) Methylaminoethanol salt of 3-S-(4,5-diphenyloxazol-2-yl)-mercaptopropionic acid (acid to alcohol ratio=2:1)  m.p. 68°–70° C
d) 2-dimethylaminoethanol salt of 3-S-(4,5-diphenyloxazol-2-yl)-mercaptopropionic acid (acid to alcohol ratio = 2:1)  m.p. 72°–73° C

EXAMPLE 9

S-(4,5-DIPHENYLOXAZOL-2-YL)-MERCAPTOACETAMIDE 12.6 g 2-thiol-4,5-diphenyloxazole and 4.67 g chloroacetamide were charged in a 500 ml, three-necked flask provided with reflux condenser and mechanical stirrer, together with 27.6 g anhydrous $K_2CO_3$ and 200 ml absolute ethanol.

The reaction mixture was refluxed for 5 hours with vigorous stirring and then filtered while still warm. The material collected on the filter was washed with 50 ml hot absolute ethanol and the hot filtrate was diluted with an equal volume of distilled water. The title compound quickly crystallized and was recovered in the amount of 9.7 g after recrystallization from ethanol. Yield = 63%; m.p.: 123°–124° C.

Analysis: Calc. for $C_{17}H_{14}O_2N_2S$: C = 65.78%; H = 4.55%; Found: C = 65.84%; H = 4.79%

EXAMPLE 10

N-(2-DIMETHYLAMINOETHYL)-S-(4,5-DIPHENYLOXAZOL-2-YL)-MERCAPTOACETAMIDE 9.3 g S-(4,5-diphenyloxazol-2-yl)-mercaptoacetic acid and 2.64 g N,N-dimethylethylendiamine dissolved in 40 ml tetrahydrofuran were treated with 7.4 g N,N'-dicyclohexylcarbodiimide in 30 ml tetrahydrofuran. The reaction mixture was kept for 15 hours at room temperature in a sealed flask under vigorous stirring. The mixture was then filtered to remove the formed N,N'-dicyclohexylurea and the filtrate was evaporated to dryness. The oily residue was redissolved in 5 ml methanol, the solution was treated with 8 ml 30% HCl alcohol solution and then 150 ml anhydrous ether were gradually added. 2.5 g N-(2-dimethylaminoethyl)-S-(4,5-diphenyloxazol-2-yl)-mercaptoacetamide hydrochloride were obtained after repeated crystallizations from a methanol-anhydrous ether mixture: m.p. 179°–182° C. Yield = 20%.

EXAMPLE 11

3-S-(4,5-DIPHENYLOXAZOL-2-YL)-MERCAPTOPROPIONAMIDE 14.6 g of the potassium salt of 2-thiol-4,5-diphenyloxazole suspended in 80 ml N,N-dimethylformamide were mixed with 5.4 g β-chloropriopionamide and the mixture was kept for 8 hours at room temperature with vigorous stirring. After filtering, diluting the filtrate with 200 ml water, recovering the separated solid and purifying by repeated crystallizations from benzene, 5.7 g 3-S-(4,5-diphenyloxazol-2-yl)-mercaptopropionamide were obtained melting at 156°–157° C. Yield 35.2%.

Analysis: Calc. for $C_{18}H_{16}O_2N_2S$: C = 66.64%; H = 4.97%; Found: C = 66.60%; H = 5.05%

The following amides according to this invention were prepared using procedures analogous to those described in Examples 9 to 11 above:

e) S-(4,5-diphenyloxazol-2-yl)-mercaptoacetomorpholide  m.p. 135°–137° C
f) S-(4,5-diphenyloxazol-2-yl)-mercaptoacetopiperidide  m.p. 102°–104° C
g) N,N-diethyl-S-(4,5-diphenyloxazol-2-yl)-mercaptoacetamide  m.p. 72°–73° C
h) N-propyl-S-(4,5-diphenyloxazol-2-yl)-mercaptoacetamide  m.p. 96°–98° C

EXAMPLE 12 a)
2-(2-DIETHYLAMINOETHYL)-THIO-4,5-DIPHENYLOXAZOLE 30.3 g 2-thiol-4,5-diphenyloxazole, 66.3 g anhydrous $K_2CO_3$ and 300 ml absolute ethanol were charged in a 1000 ml, three-necked flask provided with reflux condenser and mechanical stirrer. 25.8 g 2-diethylaminoethylchloride hydrochloride dissolved in 150 ml absolute ethanol were gradually added to the above mixture which was then refluxed for 4 hours under vigorous stirring.

The reaction mixture was then filtered while still warm and the material collected on the filter was washed with 100 ml absolute ethanol. The collected filtrates were evaporated to dryness in vacuo to give an oily residue which was then redissolved in a mixture of 200 ml ether and 200 ml distilled water. The mixture was placed in a separatory funnel in which the ethereal phase was separated, dried over anhydrous $Na_2SO_4$, filtered and evaporated to dryness in vacuo to give again an oily residue which was dissolved in 250 ml anhydrous ether. By means of addition of 25 ml 30% HCl alcohol solution, a precipitate was obtained consisting of 2-(2-diethylaminoethyl)-thio-4,5-diphenyloxazole hydrochloride. Recrystalization from a methanol-anhydrous ether mixture gave 41.17 g of a product melting at 164°–166° C. Yield 88.5%.

Analysis: Calc. for $C_{21}H_{24}ON_2S.HCl$: C = 64.84%; H = 6.48%; Found: C = 64.62%; H = 6.56% b) THE IODOMETHYLATE OF COMPOUND 12 (a) ABOVE 12 g 2-(2-diethylaminoethyl)-thio-4,5-diphenyloxazole hydrochloride were dissolved in 36 ml absolute ethanol and the solution thus obtained was treated with 14.5 g $CH_3I$ and kept at room temperature for 12 hours in a sealed flask. The crystalline quaternary salt separated from the solution which was diluted with 36 ml anhydrous ether before filtration. The reaction product was purified by recrystallization from absolute ethanol to give 15.1 g of a product melting at 203°–205° C: Yield = 89.9%

ANALYSIS: Calc. for $C_{21}H_{24}ON_2S.CH_3I$: C = 53.44%; H = 5.50%; Found: C = 53.02%; H = 5.46%

EXAMPLE 13

2-(2-AMINOETHYL)-THIO-4,5-DIPHENYLOXAZOLE 2.55 g 2-chloro-4,5-diphenyloxazole, 1.56 g cisteamine, and 3.03 g triethylamine in 20 ml absolute ethanol were refluxed for 6 hours. The mixture was cooled and the reaction product was precipitated with water.

The crystalline mass was purified by recrystallization from aqueous methanol, a small amount of N,N-dimethylformamide being added to help solution of the product in the methanolic solvent. Yield = 2.1 g (70.9%) - Melting point: 192°–193° C.

Analysis: Calc. for $C_{17}H_{16}ON_2S$: C = 68.89%; H = 5.44%; Found: C = 69.10%; H = 5.04%

The following amines according to the present invention were prepared using procedures analogous to those described in Examples 12 and 13 above:

i) 2-(2-morpholinoethyl)-thio-4,5-diphenyloxazole m.p. 226°–230° C j) 2-(2-pyrrolidinoethyl)-thio-4,5-diphenyloxazole m.p. 192°–195° C k) 2-(2-dimethylaminoethyl)-thio-4,5-diphenyloxazole hydrochloride m.p. 206°–208° C l) 2-(3-dimethylaminopropyl)-thio-4,5-diphenyloxazole hydrochloride m.p. 159°–162° C m) The iodomethylate of compound (1) above. m.p. 168°–170° C n) 2-(2-acetylaminoethyl)-thio-4,5-diphenyloxazole m.p. 108°–110° C

EXAMPLE 14

2-(2-HYDROXYETHYL)-THIO-4,5-DIPHENYLOXAZOLE 25.5 g 2-chloro-4,5-diphenyloxazole, 15.6 g 2-mercaptoethanol and 30.3 g triethylamine were dissolved in 150 ml anhydrous acetone. The solution was maintained for two hours at room temperature, then refluxed for three hours and cooled.

By addition of 500 ml distilled water an oil separated which was extracted with ether. The ethereal extract was washed twice with 5% HCl, once with 5% $K_2CO_3$, twice with distilled water and then dried over anhydrous $Na_2SO_4$.

The oily residue was redissolved in 100 ml anhydrous ether and filtered. By addition of 80 ml petroleum ether, a crystalline product consisting of 2-(2-hydroxyethyl)-thio-4,5-diphenyloxazole separated from the filtrate and was then recrystallized from an anhydrous ether-petroleum ether mixture. Yield = 22.5 g (75.8%); m.p. 54°–56° C.

Analysis: Calc. for $C_{17}H_{15}O_2NS$: C = 68.66%; H = 5.08%; Found: C = 68.77%; H = 4.72%

EXAMPLE 15

2-(3-HYDROXYPROPYL)-THIO-4,5-DIPHENYLOXAZOLE 8.73 g potassium salt of 2-thiol-4,5-diphenyloxazole and 8.34 g 3-bromo-1-propanol dissolved in 100 ml absolute ethanol were refluxed for 6 hours.

300 ml distilled water were added to the ethanol solution to redissolve the precipitated KBr, the oily product was extracted with ether and the ethereal extract was dried over anhydrous $Na_2SO_4$ and evaporated to dryness under vacuum.

The oily residue was redissolved in anhydrous ether. By addition of petroleum ether, 2-(3-hydroxypropyl)-thio-4,5-diphenyloxazole slowly crystallized. After recrystallization from an anhydrous ether-petroleum ether mixture, 6.41 g product melting at 64°–65° C were obtained. Yield - 68.7%

Analysis: Calc. for $C_{18}H_{17}O_2NS$: C = 69.22%; H = 5.50%; Found: C = 68.98%; H = 5.28%

The acute toxicity of some of the compounds of formula (I) was determined as approximate $LD_{50}$, according to the method described in Acta Pharmacol, et toxicol, 25, 345 (1967), on three groups of three "Swiss" mice.

The results are summarized in Table I.

TABLE I

| Compound of Example | Approximate $LD_{50}$ mg/kg i.p. |
|---|---|
| 2 | 220 |
| 3 | 220 |
| 9 | 1200 |
| 5 | 220 |
| 4 | 220 |

The inhibitory activity on platelet aggregation was determined for the same compounds in vitro on platelet-rich rabbit plasma prepared by collecting the blood in a plastic centrifuge tube containing enough 3.8% sodium citrate to give a concentration of 0.38 g/100 ml when mixed with the blood, and then centrifuging at 100 × g for 20 minutes.

1 ml aliquots of the thus prepared plasma were placed in a Platelet Aggregation Meter connected to a potentiometric recorder and tested according to Born, Nature (London), 194, 927 (1962).

The plasma-test compound mixtures were incubated for 10 min. at 37° C before addition of the aggregating agents, that is, Adenosine Diphosphate (ADP) or collagen.

The curves were read following the method described by O'Brien et al., Thromb. Diath. Haemorrhag. 16, 751 (1966). Slope and maximum transmission were recorded and expressed as % change with respect to controls. In the case of collagen induced platelet aggregation, the delay time ("reaction time") in seconds from the addition of the aggregating agent to the inflection of the curve was also measured and expressed as % change as above. For comparison purposes, acetylsalicylic acid (ASA) was also tested in the same conditions as the test compounds.

The results are shown in tables II and III below. Negative figures in slope and maximum transmission % changes indicate antiaggregating activity. Positive figures in delay time % changes indicate that the compound is effective in prolonging the reaction time in the collagen induced platelet aggregation test.

TABLE II

ADP (5 µg/ml) INDUCED PLATELET AGGREGATION

| Compound of Example | Concentration, µg/ml | Maximum transmission, % change | Slope, % change |
|---|---|---|---|
| 2 | 100 | −13.5 | −14.1 |
| 3 | 100 | −7.2 | −6.3 |
| 9 | 100 | −6.6 | −7.1 |
| 5 | 100 | −45.2 | −47.2 |
| 4 | 100 | +1.3 | −1.3 |
| ASA | 100 | −13.2 | −17.4 |

TABLE III

COLLAGEN (40 µg/ml) INDUCED PLATELET AGGREGATION

| Compound of Example | Concentration µg/ml | Maximum transmission, % change | Slope, % change | Delay time (reaction time) % change |
|---|---|---|---|---|
| 2 | 1.25 | −15.6 | −21.2 | +31.4 |
| 3 | 1.25 | −76.6 | −78.3 | +36.2 |
| 9 | 1.25 | −12.3 | −18.4 | +7.2 |
| 5 | 1.25 | −67.7 | −72.5 | +28.3 |
| 4 | 1.25 | −73.3 | −77.1 | +26.3 |
| ASA | 1.25 | −15.2 | −22.1 | +2.4 |

The present compounds of general formula (I) can be formulated into suitable pharmaceutical dosage forms, e.g., coated or uncoated tablets, capsules, syrups, suspensions, suppositories, etc., by mixing them with pharmaceutically acceptable excipients, carriers or diluents, in accordance with methods well known in the art. The present compounds, salts or pharmaceutical compositions may all be used therapeutically.

Thus, the invention also includes a method for inhibiting platelet aggregation in blood, which method comprises adding to the blood or administering to an animal an effective amount of a compound, salt or pharmaceutical composition in accordance with the present invention.

The following Example shows a typical preparation of capsules in accordance with the invention.

EXAMPLE 16

Capsules containing 100 mg of the active substance and having the following composition were prepared:

| | |
|---|---|
| S-(4,5-diphenyloxazol-2-yl)-mercaptoacetamide | 100 mg |
| Glycocoll | 50 mg |
| Starch | 100 mg |
| Lactose | 100 mg |
| Talc | 20 mg |
| Magnesium Stearate | 10 mg |
| | 380 mg |

In human therapy, the preferred mode of administration is oral and the daily dosage can be in the range of 200–800 mg, preferably about 600 mg/day.

I claim:

1. A compound of the formula

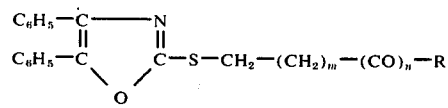

wherein $m$ is 0, 1 or 2; $n$ is 0 or 1; R is a hydroxy, amino, alkylamino, morpholino, piperidino, pyrrolidino, aminoalkoxy, or alkylaminoalkoxy radical, the alkyl chains in said radicals having 1–4 carbon atoms, and provided that R is not hydroxy when $n$ is 1; and the pharmaceutically acceptable addition salts thereof.

2. S-(4,5-Diphenyloxazol-2-yl)-mercaptocarboxylic acid amide according to claim 1 wherein $n$ is 1 and R is said amino, alkylamino, morpholino, piperidino or pyrrolidino radical, and the pharmaceutically acceptable acid addition salts thereof.

3. S-(4,5-Diphenyloxazol-2-yl)-mercaptocarboxylic acid ester according to claim 1 wherein $n$ is 1 and R is said aminoalkoxy or alkylaminoalkoxy radical, and the pharmaceutically acceptable acid addition salts thereof.

4. 2-Aminoalkylthio-4,5-diphenyloxazole according to claim 1 wherein $n$ is 0 and R is said amino, alkylamino morpholino, piperidino or pyrrolidino radical, and pharmaceutically acceptable acid addition salts thereof.

5. 2-Oxyalkylthio-4,5-diphenyloxazole of the formula:

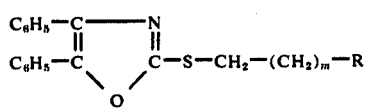
wherein *m* is 0, 1 or 2 and R is hydroxy or alkoxy of 1 to 4 carbon atoms.
6. An addition salt of S-(4,5-diphenyloxazol-2-yl)-mercaptocarboxylic acid of the formula:
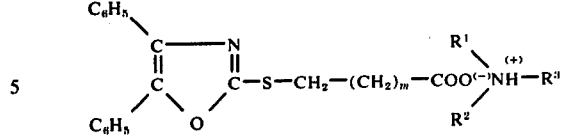
wherein *m* is 0, 1 or 2 and $R^1$, $R^2$ and $R^3$ are each hydrogen or an alkyl or hydroxyalkyl having from 1 to 4 carbon atoms.
* * * * *